United States Patent [19]
Moise

[11] Patent Number: 4,779,614
[45] Date of Patent: Oct. 25, 1988

[54] MAGNETICALLY SUSPENDED ROTOR AXIAL FLOW BLOOD PUMP

[75] Inventor: John C. Moise, Carmichael, Calif.

[73] Assignee: Nimbus Medical, Inc., Rancho Cordova, Calif.

[21] Appl. No.: 36,304

[22] Filed: Apr. 9, 1987

[51] Int. Cl.$^4$ ............................................. A61B 19/00
[52] U.S. Cl. ........................................ 600/16; 604/9; 604/151; 604/67; 415/DIG. 4; 417/356; 623/3
[58] Field of Search ............................ 604/65, 67, 151; 415/DIG. 4; 128/1 D, DIG. 3; 623/3; 417/352-356

[56] References Cited

U.S. PATENT DOCUMENTS

| | | | |
|---|---|---|---|
| 4,123,666 | 10/1978 | Miller | 417/356 |
| 4,155,022 | 5/1979 | Crockett | 415/DIG. 4 |
| 4,625,712 | 12/1986 | Wampler | 128/1 D |
| 4,688,998 | 8/1987 | Olsen | 417/356 |

*Primary Examiner*—C. Fred Rosenbaum
*Assistant Examiner*—Gene B. Kartchner
*Attorney, Agent, or Firm*—Weissenberger & Peterson

[57] ABSTRACT

An implantable axial flow blood pump maximizes the blood flow while minimizing the dimensions of the pump. By magnetically suspending a rotor of relatively small diameter coaxially in a cylindrical blood conduit of substantially larger inner diameter, an adequate flow area through the pump is provided, and the need for bearings, lubrication and seal purging fluid is eliminated. This is made possible by the use of neodymium-boron-iron rotor magnets which allow a substantial gap between the static motor armature and the rotor. The rotor is simultaneously torqued and maintained in a position coaxial with the blood conduit by individually varying the current in the armature windings while they are being commutated. The position of the rotor axis is accurately sensed by placing magnetically permeable strips into opposite ends of the pump stator blades in such a manner that they transmit to Hall sensors variations in an annular magnetic field surrounding the rotor adjacent the ends of the pump stator blades.

9 Claims, 3 Drawing Sheets

4,779,614

MAGNETICALLY SUSPENDED ROTOR AXIAL FLOW BLOOD PUMP

FIELD OF THE INVENTION

This invention relates to magnetically suspended rotor axial flow blood pumps, and more particularly to an implantable pump for chronic heart assist.

BACKGROUND OF THE INVENTION

U.S. Pat. No. 4,625,712 discloses a miniature high-speed axial flow intravascular blood pump percutaneously inserted and powered through a drive cable from outside the patient's body for emergency or other temporary heart assist.

It would be highly desirable to provide compact pumps of this type for patients needing long-term (chronic) heart assist. Such pumps are much more anatomically compatible than the large implantable heart assist pumps currently being developed. They also have the potential for much lower manufacturing costs.

Unfortunately, the design of fully implantable axial flow blood pumps with a self-contained motor presents major problems. The approach discussed in U.S. Pat. No. 4,625,712 utilizes the fluid flow of a purged fluid seal to prevent entry of blood elements into the pump. Supplying such a purge fluid from within the body presents major technical challenges. Percutaneous supply of the purge fluid degrades the patient's quality of life and provides a potential infection entry site.

SUMMARY OF THE INVENTION

The pump of the present invention solves the above-stated problems by providing an axial flow pump with a magnetically suspended rotor in which both alignment and torque are provided by a pair of axially spaced sets of stator armatures and corresponding permanent magnets in the rotor. The position and inclination of the rotor axis are sensed in the pump of the invention by sensors imbedded in the stator blades of the pump.

The use of rare earth magnetic materials in the rotor makes it possible to maintain a substantial gap between the poles of the stator armature and the rotor so as to provide a substantial blood flow path area, yet the location of the rotor position sensors in the pump stator blades makes it possible to sense extremely small position changes of the rotor axis very rapidly.

It is therefore the object of this invention to provide a miniature self-contained electric axial flow blood pump.

It is another object of the invention to accomplish this result by using a magnetically suspended rotor with a substantial gap between the rotor and the stator poles, and by placing the sensing elements of the axis position sensors inside the pump stator blades.

DESCRIPTION OF THE PREFERRED EMBODIMENT

Figure 1:
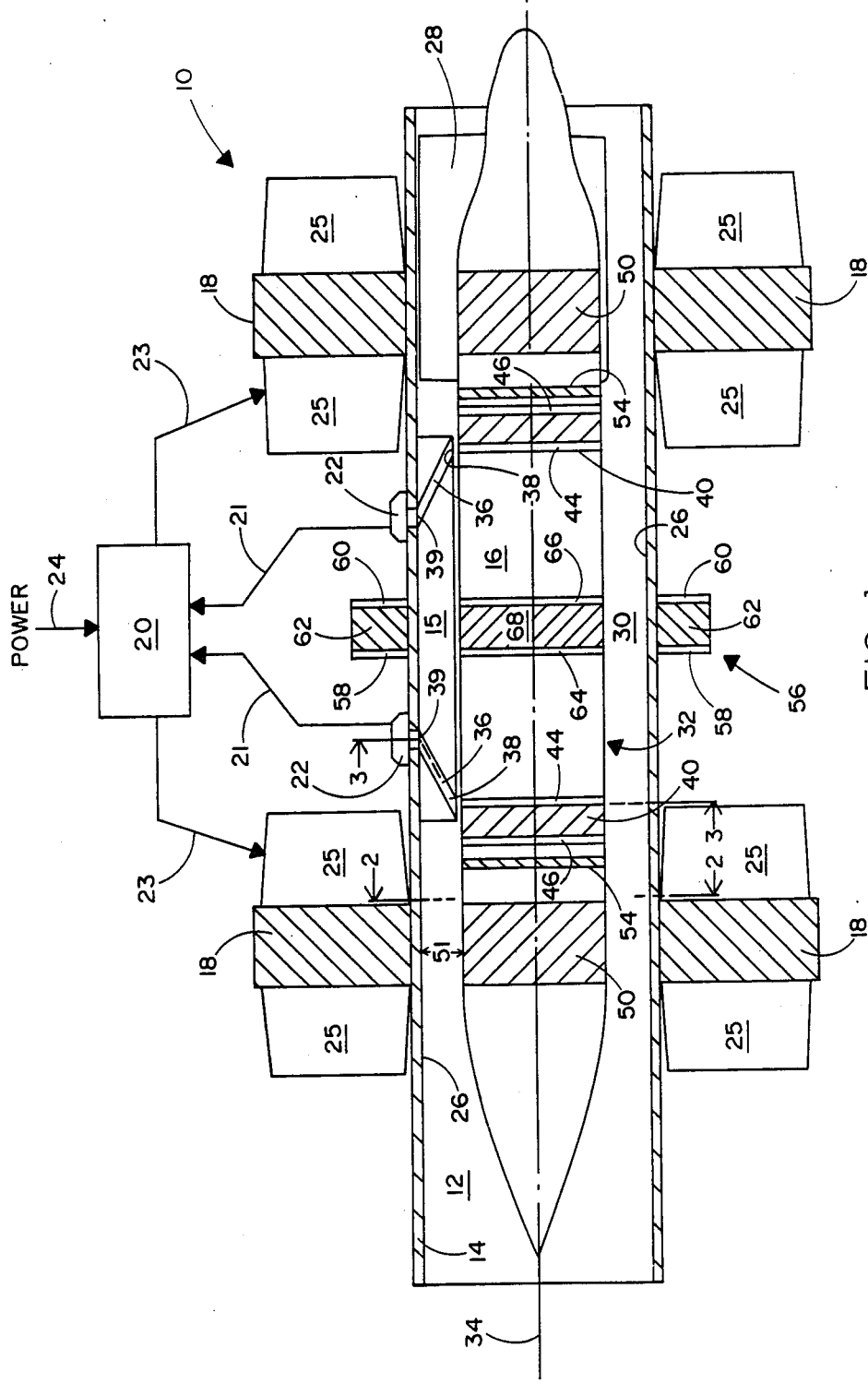
FIG. 1 is an axial section, partially in schematic form, of an axial flow blood pump constructed in accordance with this invention.

FIG. 1 shows, in somewhat schematic form, a blood pump 10 constructed in accordance with this invention. The pump components external to the blood flow path 12 are mounted on a cylindrical blood conduit 14. The internal components of the pump 10, which are immersed in the blood flow in path 12, consist of pump stator blades 15 and a magnetically suspended rotor 16. Motor armatures 18 are positioned at each end of pump 10. Appropriate electronic and microprocessor circuitry 20 may be positioned at any convenient location on the pump 10 or elsewhere, and is shown in FIG. 1 as connected to the pump 10 by inputs 21 and outputs 23. Axially spaced flux sensors 22 are positioned between the armatures 18 on the outside of the blood conduit 14. Electric power is supplied to the pump 10 by conventional means such as wiring 24 leading to an appropriate percutaneous power supply or a transcutaneous transformer and rectifier (not shown). The electronic and microprocessor circuits 20 control the currents in the various windings 25 of the armatures 18 in a manner described below.

Three or more pump stator blades 15 are suspended from the inner surface 26 of the blood conduit 14. The rotor 16 preferably carries a corresponding number of pump rotor blades 28. The pump stator blades 15 and the pump rotor blades 28 cooperate to form a pumping stage in accordance with well-known principles of axial flow pump design.

In order to avoid the need for close-tolerance bearings and for a seal which would require a supply of fluid other than blood, the rotor 16 of this invention is magnetically suspended in the blood stream and makes no physical contact with the blood conduit 14. In fact, as will be seen in FIG. 1, an annular portion 30 of the blood flow path 12 having a substantial cross-sectional area exists between the hub 32 of rotor 16 and the inner wall 26 of blood conduit 14.

Because of the close clearance between the rotor 16 and the pump stator blades 15, and also because of the strong dynamic forces operating on the rotor 16 at high rotary speeds, it is essential that the axis 34 of rotor 16 be maintained in a precisely aligned and centered position at all times. The alignment and centering of the rotor is accomplished by the armatures 18 in a manner hereafter described.

Figure 3:
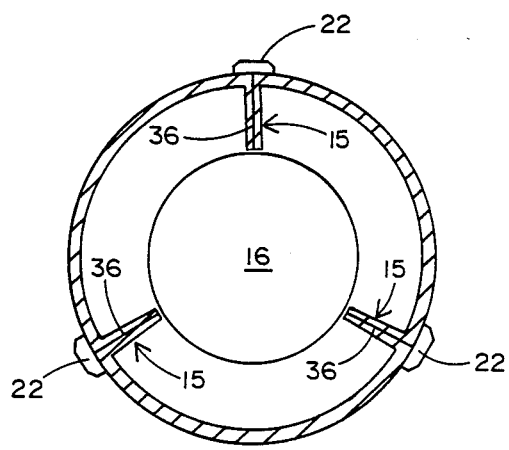
FIG. 3 is a fragmentary section along line 3—3 of FIG. 1.

Positional information regarding the centering and inclination or alignment of the rotor axis could theoretically be gleaned from measurements taken outside the blood circuit 14, but due to the substantial gap between the inner surface 26 of blood conduit 14 and the rotor 16, that measurement is not sufficiently precise. For this reason, the invention provides thin sensor strips 36 of highly permeable magnetic material such as soft iron embedded in each of the three (FIG. 3) or more pump stator blades 15 whose inner ends 38 are closely adjacent to the rotor 16, and whose outer ends 39 are connected to appropriate conventional flux sensors 22, 23 such as Hall sensors.

Figure 4:
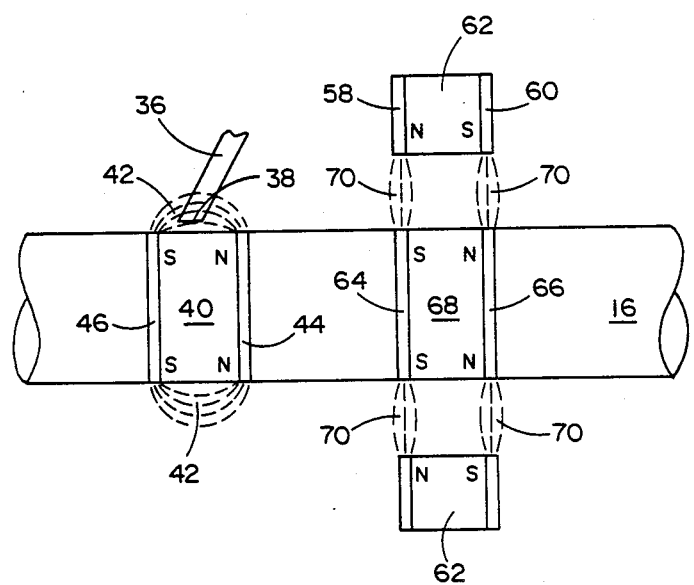
FIG. 4 is a schematic view illustrating the functioning of the position sensing and axial centering features of the device of FIG. 1.

The suspended rotor 16 carries a pair of spaced sensor magnets 40 whose disk-shaped pole pieces 44, 46 are disposed transversely to the rotor axis 34. If, for example, pole piece 44 is a north pole and pole piece 46 is a south pole, a flux field 42 will exist between the pole pieces 44, 46 radially outwardly along the periphery of the rotor 16 (FIG. 4). The field 42 rapidly weakens in a radially outward direction. Consequently, the inner ends 38 of the sensor strips 36 are immersed in a field whose strength is a function of the gap between the pump stator blade 15 and the rotor 16 at the location of end 38. The sensor strips 36 transmit these field strength indications to their respective flux sensors 22. Because of the proximity of ends 38 to the periphery of rotor 16, a small change in the position of rotor axis 34 causes a relatively large change in the flux sensed by sensor strips 36 and therefore by the flux sensors 22. The flux sensors 22 in turn provide signals to the circuitry 20 which translates them by conventional triangulation programming (cf. FIG. 2) into centering and alignment data for controlling the currents in the individual windings of armatures 18.

Figure 2:
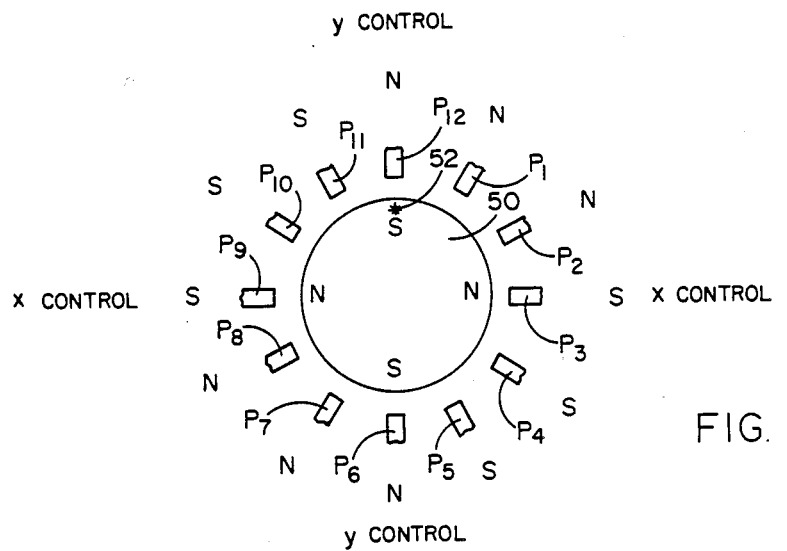
FIG. 2 is a schematic section along line 2—2 of FIG. 1.

As schematically shown in FIG. 2, each of the stator armatures 18 may have twelve poles $P_1$ through $P_{12}$ disposed equidistantly about rotor 16. In the areas of the armatures 18, the rotor 16 contains a rotor magnet 50, preferably of a rare earth material such as a neodymium-boron-iron alloy which is orthogonally polarized as shown in FIG. 2. The use of a rare earth magnetic material in the rotor magnet 50 allows a substantial gap 51 (FIG. 1) to exist between the poles P of armatures 18 and the hub 32 of rotor 16 without substantial loss of motive power.

In the rotor position of FIG. 2, reducing the current in the winding of pole $P_{12}$ and/or increasing it in the winding of pole $P_6$ will move the rotor downward, while reducing the current at $P_3$ and/or increasing it at $P_9$ will move it to the left. Opposite actions will have the opposite effect. At the same time, the indicated polarities of poles $P_1$, $P_2$, $P_4$, $P_5$, $P_7$, $P_8$, $P_{10}$ and $P_{11}$ cause the rotor 16 to rotate in a clockwise direction.

When point 52 on the rotor has moved to a position half way between poles $P_{12}$ and $P_1$, the polarity of the currents in the windings 25 of the armatures 18 is commutated clockwise by thirty degrees so that $P_1$, $P_4$, $P_7$ and $P_{10}$ become the positioning poles while the remaining poles become the torquing poles.

The control circuitry 20 controls the speed of the rotor 16 by controlling the commutation sequence, and it controls the centering and alignment of the rotor axis 34 by selectively varying the current in the appropriate windings 25 of armatures 18.

It will be noted that the construction described herein, because it does not require any separate alignment coils, nor any position sensors outside the existing pump stator blades, allows the pump 10 to be made quite short. The stator blades 15 are relatively long not only in order to space the sensor strips 36 as far apart as possible for improved tilt control, but also because long stator blades are physiologically advantageous in reducing turbulence in the blood flow. The resulting shortness of the pump 10 is a distinct advantage with respect to anatomic compatibility. Magnetic interference between the rotor magnets 50 and the sensor magnets 40 is prevented by the use of magnetic shields 54.

Basically, the self-centering action of the rotor magnets 50 maintains the proper position of rotor 16 in the axial direction. This is true even when the pump 10 is not energized because the rotor magnets 50 tend to move toward the iron of the armatures 18. However, due to the relatively large gaps 51 required to accommodate the blood flow annulus 30, the spring rate associated with the axial stability of the interaction between the rotor magnets 50 and the armature 18 may be low enough in certain practical applications of the invention to allow greater than desirable axial motion of the suspended rotor 16 when its pressure differential changes as the heart alternates between systole and diastole. A higher axial spring rate can be built into the configuration of FIG. 1 by utilizing one or more centering magnet sets 56 located midway between the armatures 18 (or, for a plurality of sets 56, equidistantly from that midpoint) to avoid the imposition of any tilting forces on the axis 34.

FIG. 4 illustrates the magnetic fields involved in the operation of the sensor strips 36 and the centering magnet set 56. The ends 38 of the sensor strips 36 are immersed in a generally axially directed field 42 extending between the pole pieces 44, 46 of sensor magnets 40. By contrast, in the centering magnet set 56, the pole pieces 58, 60 of annular magnets 62 on the blood conduit 14 cooperate with the pole pieces 64, 66 of disk magnets 68 to create radially directed fields 70 which strongly resist any axial movement of rotor 16 without substantially impeding the radial or rotational movement imparted to rotor 16 by the interaction of armatures 18 and rotor magnets 50.

It will be seen that the present invention provides an extremely compact implantable blood pump of simple and rugged construction which produces a large blood flow with a pump of highly anatomically compatible dimensions. The pump 10 inherently has high reliability and long life due to the absence of any contact between mutually movable mechanical elements during operation.

I claim:

1. An implantable axial flow blood pump, comprising:
   (a) a stator defining a substantially cylindrical blood conduit;
   (b) at least three pump stator blades extending inwardly from the inner surface of said blood conduit;
   (c) a substantially cylindrical rotor rotatable within said blood conduit and having a hub and a plurality of rotor blades;
   (d) the hub of said rotor being spaced from the inner surface of said blood conduit a sufficient distance to define between said inner blood conduit surface and said hub an annular space sufficient to accommodate the blood flow through said pump;
   (e) said rotor being magnetically suspended coaxially with said blood conduit, but out of physical contact with said stator, during the operation of said pump,
   (f) sensing means associated with said blood conduit for sensing the position of the axis of said rotor with respect to the axis of said blood conduit;
   (g) positioning means on said blood conduit responsive to said sensing means for maintaining said rotor in a position coaxial with said blood conduit; and
   (h) torquing means on said blood conduit for imparting a rotary torque to said rotor.

2. The blood pump of claim 1, in which said positioning and torquing means are jointly embodied by providing in said rotor a permanent magnet, and disposing outwardly of said blood conduit an armature having a plurality of poles surrounding said rotor magnet, each of said poles being energized by a winding individually controllable with respect to current and polarity.

3. The blood pump of claim 2, in wich said positioning and torquing means consist of a pair of axially spaced armatures and a pair of rotor magnets axially aligned therewith.

4. The blood pump of claim 2, further comprising circuit means responsive to said sensing means for controlling said current and simultaneously commutating said windings.

5. The blood pump of claim 2, further comprising at least one centering magnet set on said blood conduit and in said rotor for urging said rotor into an axial position in which said rotor magnet is axially aligned with said armature.

6. The blood pump of claim 5, in which there are two axially spaced armatures, and said centering magnet sets are disposed symmetrically with respect to the midpoint between said armatures.

7. The blood pump of claim 1, in which said rotor includes axially spaced pole pieces of opposite polarity to produce annular magnetic fields around said rotor adjacent the ends of said pump stator blades, and said sensor means include flux sensors external of said blood conduit and highly permeable magnetic elements carried by said pump stator blades at each end thereof, said highly permeable magnetic elements extending between said magnetic fields and said flux sensors.

8. The blood pump of claim 1, in which said rotor includes rotor magnets formed of a rare earth magnetic material.

9. The blood pump of claim 8, in which said rare earth magnetic material is a neodymium-boron-iron alloy.

* * * * *